US006854862B1

(12) United States Patent
Hopf (10) Patent No.: US 6,854,862 B1
(45) Date of Patent: Feb. 15, 2005

(54) ADJUSTABLE LIGHT

(76) Inventor: Steven L. Hopf, 4071 Maplewood Pl., Riverside, CA (US) 92506

(*) Notice: Subject to any disclaimer, the term of this patent is extended or adjusted under 35 U.S.C. 154(b) by 0 days.

(21) Appl. No.: 10/350,442

(22) Filed: Jan. 24, 2003

(51) Int. Cl.[7] .................................................. F21S 4/00
(52) U.S. Cl. ....................... 362/220; 362/250; 362/270; 362/287; 362/418
(58) Field of Search ................................ 362/220, 250, 362/270, 287, 285, 418, 419, 427, 402, 421

(56) References Cited

U.S. PATENT DOCUMENTS

| | | | |
|---|---|---|---|
| 1,656,777 A | | 1/1928 | Dennis |
| 3,604,913 A | * | 9/1971 | Crete ............................ 362/8 |
| 4,463,413 A | | 7/1984 | Shirley ....................... 362/401 |
| 4,803,606 A | | 2/1989 | Rotter ........................ 362/250 |
| 5,023,755 A | | 6/1991 | Rosenberg ................... 362/12 |
| 5,103,384 A | * | 4/1992 | Drohan ....................... 362/191 |
| 5,126,928 A | | 6/1992 | Hughes ....................... 362/287 |
| 5,424,931 A | * | 6/1995 | Wheeler ..................... 362/418 |
| 5,448,464 A | | 9/1995 | Moss ......................... 362/401 |
| 5,675,417 A | * | 10/1997 | Ventura et al. ............. 356/600 |
| 5,848,834 A | * | 12/1998 | Kerr ............................ 362/190 |
| 6,000,823 A | * | 12/1999 | Desmond et al. ........... 362/494 |
| 6,019,484 A | | 2/2000 | Seyler ........................ 362/287 |

* cited by examiner

Primary Examiner—Sandra O'Shea
Assistant Examiner—Mark Tsidulko (57) ABSTRACT

An adjustable light includes a knock down base frame, a vertical frame, which supports a boom arm, which in turn supports a light fixture. The light fixture is supported on the boom arm by a fixture mount that provides five degrees of freedom of movement of the light fixture relative to the boom arm. The boom arm is pivotally mounted to the vertically adjustable frame, thereby providing two additional degrees of freedom to the light fixture relative to the ground. The base frame includes two legs that are movably secured to the base frame. The base frame and the legs include wheels, the wheel supports being movably mounted to the frame and legs to allow for free movement on any planar surface on which the adjustable light is supported. The boom arm and the shield of the light fixture include bumpers to prevent damage by inadvertent contact to a surface. The lens in the fixture is replaceable to allow the user to use different lenses as dictated by the job requirements. A typical lens includes a substantially opaque section approximately one inch wide that is positioned in the center of the lens and runs the length of the lens.

35 Claims, 7 Drawing Sheets

ADJUSTABLE LIGHT

FIELD OF THE INVENTION

The present invention generally relates to lighting devices. More specifically, the present invention relates to adjustable lighting devices used in a work environment.

BACKGROUND OF THE INVENTION

Shop lights are an integral part of industry from large-scale production to small shops. Proper vision is imperative to quality work. This is never more important than in the area of dent removal on automobile bodies. In some light a dent can be obvious, yet in other light not visible at all. What the technician needs to do is create a shadow by providing an angle of incident of the light rays to properly view the dent. The light is also used to guide the technician in the placement of the appropriate dent removal tool and guide him in the force application to remove the dent without causing additional damage to the vehicle's body or paint. Positioning the light fixture to obtain the proper angle of incident requires a stable but greatly adjustable light stand supporting the fixture. Fine adjustments need to be made with minimal effort in that the technician's eye must be primarily trained on the area of the dent, and not concentrating on the light stand.

The frame is preferably able to "knock down" to provide inexpensive shipping and storage capabilities. The frame must allow the light to adjust to a variety of positions and angles with several degrees of freedom including the overall height, angle and pitch of the light fixture. The lens is preferably interchangeable to allow different tints and black-out areas, which assist the technician in creating shadows. Finally the product is preferably lightweight, thus making it easy to maneuver and adjust.

SUMMARY OF THE INVENTION

In one aspect, the invention features a base frame with an adjustable height vertical frame, which is releaseably mounted to the base frame. A boom arm is pivotally mounted to an upper portion of the vertical frame and includes a clamp lock. This lock provides an infinitely adjustable position of locking of the boom arm on the vertical frame. A light fixture; is attached to a fixture mount that is slideably and rotateably mounted on the boom arm.

The base frame may include at least two legs that are movably mounted to the base frame. The base frame and the legs may include at least two wheels to facilitate transport of the device. The wheels are preferably movably (pivotally) mounted to the base frame and legs. The clamp lock is comprised of a pair of concave pressure plates, a threaded fastener and a cap handle. The boom arm includes an end disk positioned at one end thereof, the end disk being captured between a pair of ears on the vertical frame, the pair of concave pressure plates being positioned on the outside of, and adjacent to, the pair of ears.

The light includes a bumper strip mounted to a peripheral edge of a lamp shield and the boom arm includes a bumper pad positioned on a distal end thereof. The fixture mount supports the light fixture by a ball and socket joint and the mount preferably includes a split collar and a tension device, such as a threaded fastener, enabling adjustable tension on the ball of the ball and socket joint. The fixture mount includes a friction lock enabling the fixture mount to be releaseably positioned on the boom arm.

The light fixture includes a shield with a base angle between 20° and 30° relative to a lens and optimally 25° relative to the lens. The light fixture includes a lens with a substantially opaque area in the center thereof and runs the length of the lens. This substantially opaque area is between 0.75 inches and 1.25 inches wide and is preferably one inch wide.

In another aspect, the invention includes a method of using an adjustable light including the steps of providing a device as previously disclosed, adjusting the height of the vertical frame, adjusting the angle of the boom arm relative to said vertical frame, adjusting the position of the light fixture by movement of the fixture mount on the boom arm and positioning the light fixture on the fixture mount.

BRIEF DESCRIPTION OF THE DRAWINGS

The foregoing and other objects of this invention, the various features thereof, as well as the invention itself, may be more fully understood from the following description, when read together with the accompanying drawings, described.

For the most part, and as will be apparent when referring to the figures, when an item is used unchanged in more than one figure, it is identified by the same alphanumeric reference indicator in all figures.

DETAILED DESCRIPTION OF THE PREFERRED EMBODIMENT

Figure 1:
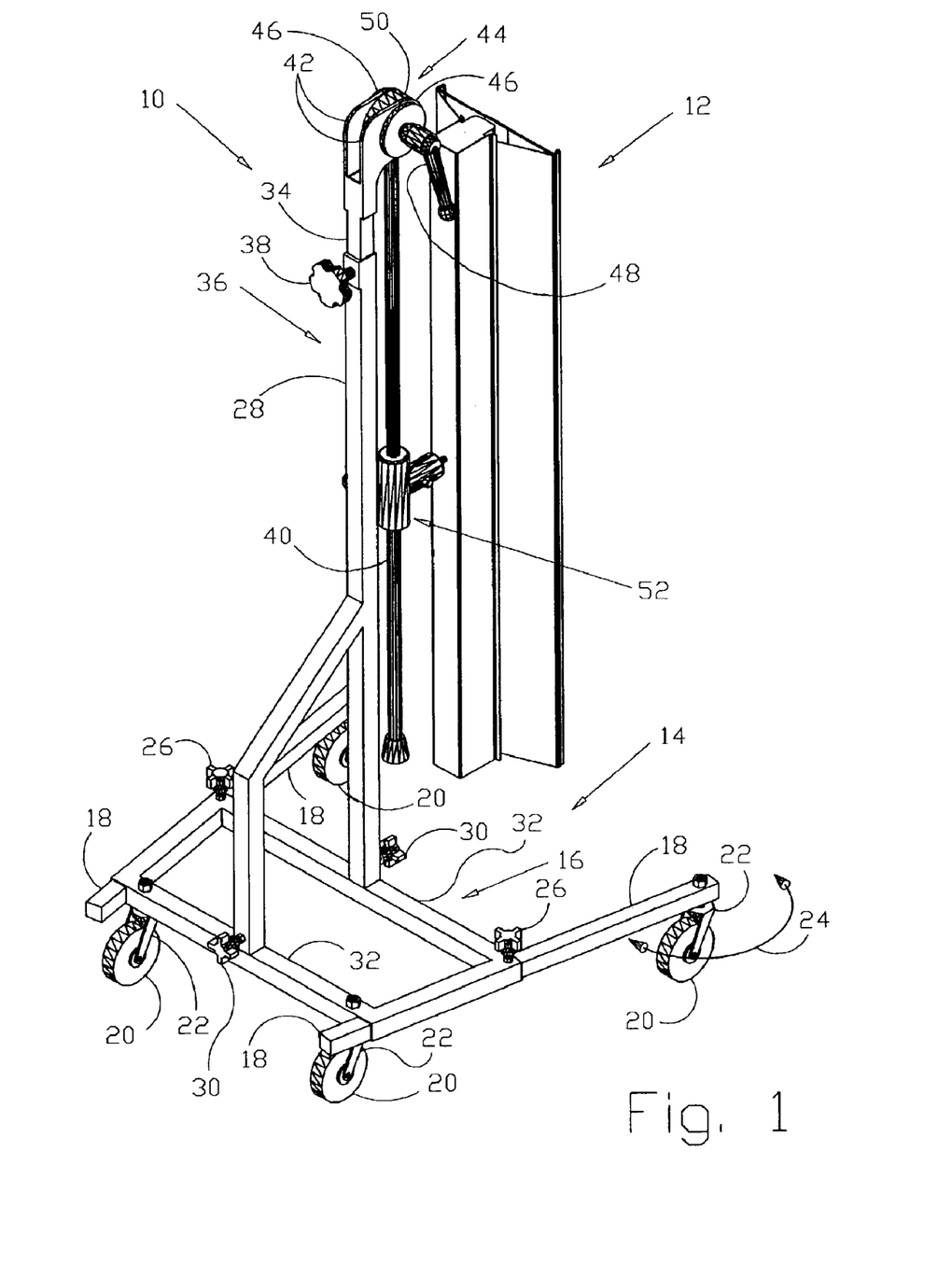
FIG. 1 is an isometric view of an adjustable light in a stored position, the light produced in accordance with the present invention.

The present invention is an adjustable light with specific applications to industry, in particular the area of automotive dent removal. Many of the advantages of this light are noted as advantageous to a variety of other applications such as light stands used in photography but the emphasis in this disclosure will be in the area of the light function as it relates to automotive dent removal. The critical advantage to the invention as disclosed is the adjustment capability of the light fixture by the capability of the framework. Referring to the drawings, FIG. 1 shows an adjustable light 10 in a compact position. The key element of the device is the light fixture 12. The detail of this fixture 12 will be disclosed later in the text, but a critical advantage of the light 10 is the capability to position the fixture 12 in a great variety of positions relative to the base 14.

It is many times advantageous for a product to "knock down". Here the base 14 is shown as being comprised of a base frame 16 and two legs 18. The legs 18 are movably mounted through the base frame 16 to allow for adjustment of the positioning of the legs 18 as well as the removal of the legs 18 for shipping or storage. This disassembly or reduced size framework is part of the "knock down" feature. Mobility is provided to the device 10 by the addition of wheels 20 on the base frame 16 and legs 18. These wheels 20 include a rotateably mounted wheel supports 22 that allow for movement, preferably 360° of rotation of the support 22 and associated wheel 20 relative to the frame 14. The arrow 24 illustrates the rotation of the wheels 20 by the wheel supports 22. Screw knobs 26 are comprised of a handle with a threaded end. The receiving portion (on the frame 16) has a threaded insert that receives the treaded end. The tip of the threaded end can be pressed against the leg 18 to infinitely adjust and hold by friction the leg 18 at any position relative to the base frame 16 within the physical parameters of each.

A vertical frame receiver 28 is received by the base frame 16 and secured by two additional screw knobs 30. The base frame 16 includes a pair of vertical studs (not shown) that are mounted to the crossbars 32 of the base frame 16. These studs are used as a support and a base to apply a load from the screw knobs 30 to lock the vertical frame receiver 28 onto the base 14. The vertical frame stem 34 is received by the vertical frame receiver 28, together comprising an adjustable height vertical frame 36. The movement of the stem 34 relative to the receiver 28 and secured by the upper screw knob 38 provides vertical positioning of the fixture 12.

Angular adjustment is provided by a boom arm 40 that is pivotally mounted to ears 42 the upper end of the vertical frame 36, specifically on the frame stem 34. The pivotal mounting includes a clamp lock 44. The clamp lock 44 includes a pair of pressure plates 46 that are pressed together by a cap handle 48. Located between the ears 42 is an end disk 50 mounted to an end of the boom arm 40. The compression of the plates 46 of the clamp lock 44 on the ears 42, on the end disk 50 of the boom arm 40 secures the boom arm 40 into any angular position of the boom arm 40 relative to the vertical frame 36. The fixture 12 is movably secured to the boom arm 40 by a fixture mount 52. The fixture mount 52 enables the fixture 12 to be positioned along the longitudinal length of the boom arm 40 as well as to rotate around the long axis of the boom arm 40. This combination gives additional height and angular position adjustment to the fixture 12.

Figure 2:
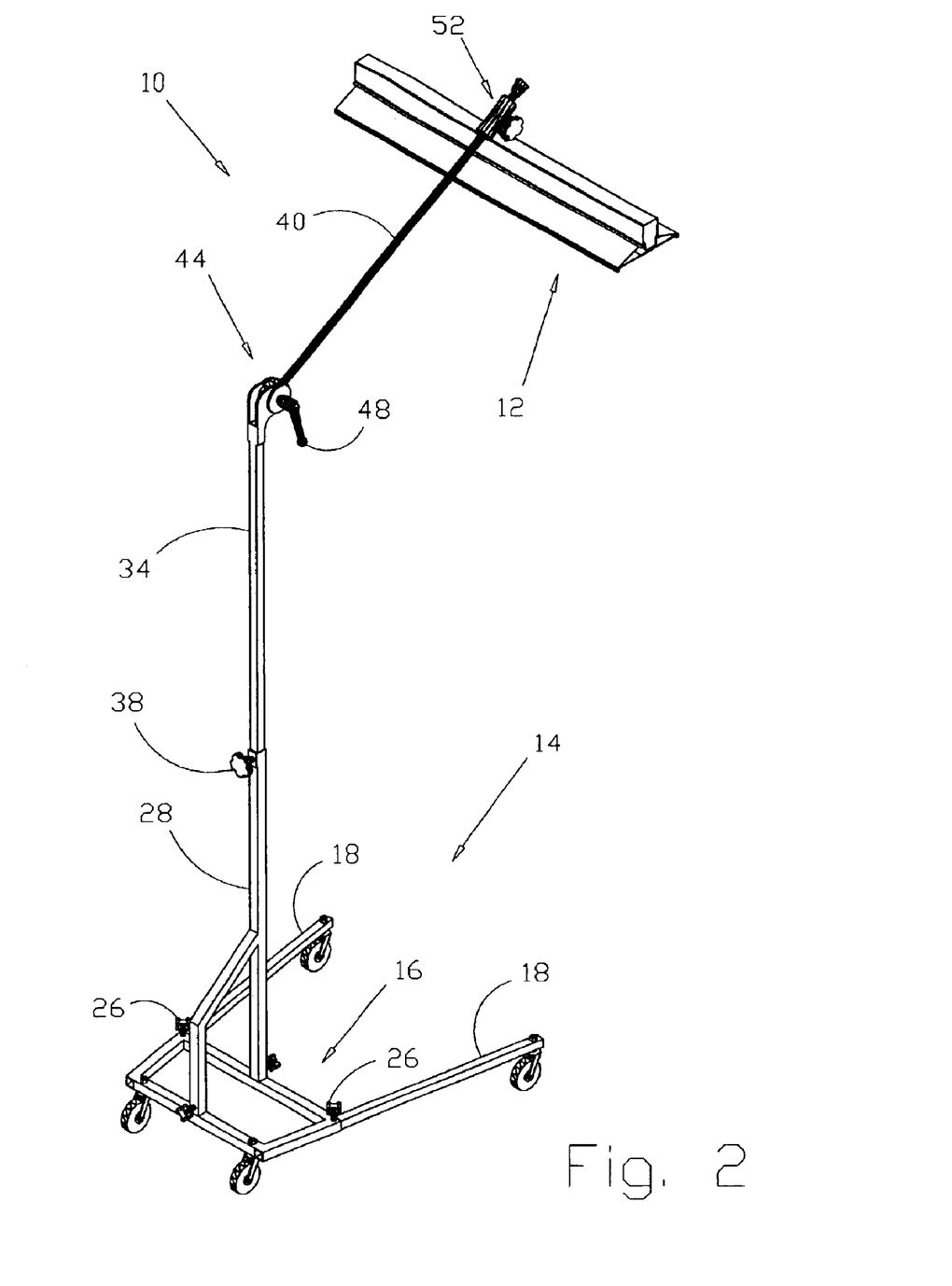
FIG. 2 is an isometric view of an adjustable light in an extended position, the light produced in accordance with the present invention.

As a contrast, the device 10 is shown in an extended position in FIG. 2. The boom arm 40 is rotated up and out away from the base 14 and locked in place with the clamp lock 44. The fixture 12 has been extended toward the end of the boom arm 40 by use of the fixture mount 52. The frame stem 34 is extended toward the end of the vertical frame receiver 28 and secured in place by the upper screw knob 38. With the vertical and horizontal displacement of the center of gravity of the device 12 relative to that shown in FIG. 1, the legs 18 have been extended out away from the base frame 16 to increase the stability of the device 10.

Figure 3:
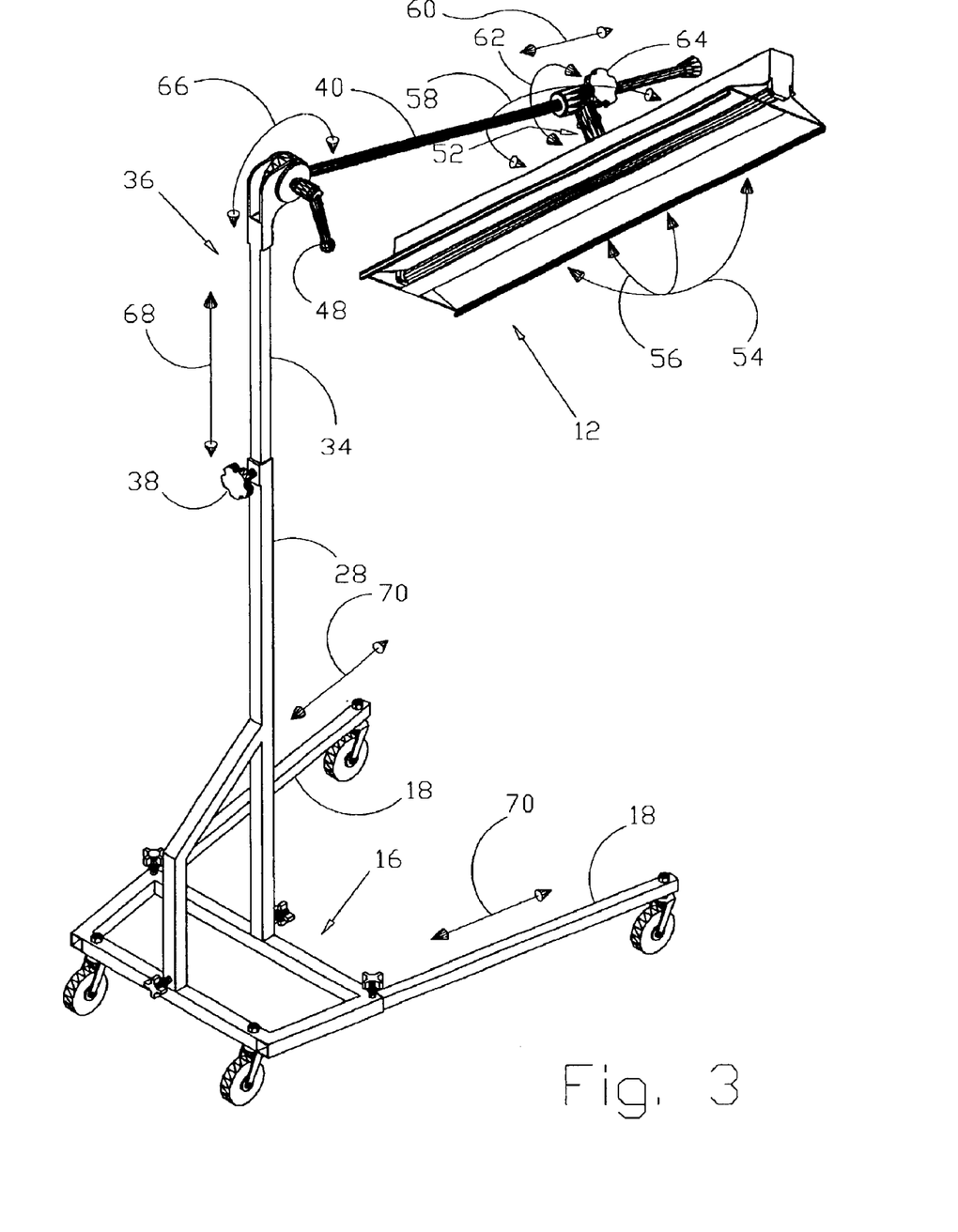
FIG. 3 is an isometric view of an adjustable light as it would be typically used and showing the degrees of freedom of movement of the light fixture and legs, the light produced in accordance with the present invention.

The adjustment capabilities are shown in FIG. 3. The fixture 12 is mounted to the fixture mount 52 by a ball and socket joint. This will be further described in greater detail later in the text. The ball and socket allows for a change in the tilt angle (along the long dimension) of the fixture 12 as depicted by the first arrow 54, as well as the pitch angle (along the short dimension) of the fixture 12 as shown by the second arrow 56. This joint also allows for movement about any axis perpendicular to the top of the fixture 12. This is depicted by the third arrow 58. The ball and socket joint on the top of the fixture 12, as it couples with the fixture mount 52, provides for three degrees of freedom of movement or adjustment of the fixture 12. The fixture mount 52 as it articulates with the boom arm 40, allows for linear adjustment along the long axis of the boom arm 40, as shown by the fourth arrow 60. By using a round or cylindrical structure for the boom of the boom arm 40, the fixture mount 52 can also be made to rotate about the long axis of the boom arm 40, as shown by the fifth arrow 62. Both the angular orientation and the linear positioning are adjusted by unscrewing the fixture knob 64 adjusting the fixture to the position desired and then tightening the fixture knob 64, providing sufficient friction between the tip of the knob 64 and the boom arm 40. Thus, with this arrangement of the fixture mount 52 on the boom arm 40 and the fixture mount 52 to the fixture 12, a total of five degrees of freedom are realized. The boom arm 40 is provided with angular adjustment that can be secured by way of the clamp lock 44. A sixth arrow 66 illustrates this angular adjustment. The final adjustment of the fixture 12 position is shown by the seventh arrow 68, which demonstrates the vertical height adjustment of the stem 34 in the frame receiver 28, which is secured by the upper screw knob 38. These additional two degrees of freedom are added to the five provided by the fixture mount 52 to yield a total of seven degrees of freedom of adjustment of the fixture 12.

With reasonable component lengths a stand can be approximately four feet high in a stored state and extend to over nine feet high with three feet of horizontal displacement from the base. The fixture can also be positioned to face up, down, or to either side and rotated horizontally, vertically or anywhere in between. Any instability is taken care of by the adjustment of the legs 18 relative to the base frame 16. The leg arrows 70 show this adjustment.

Figure 4:
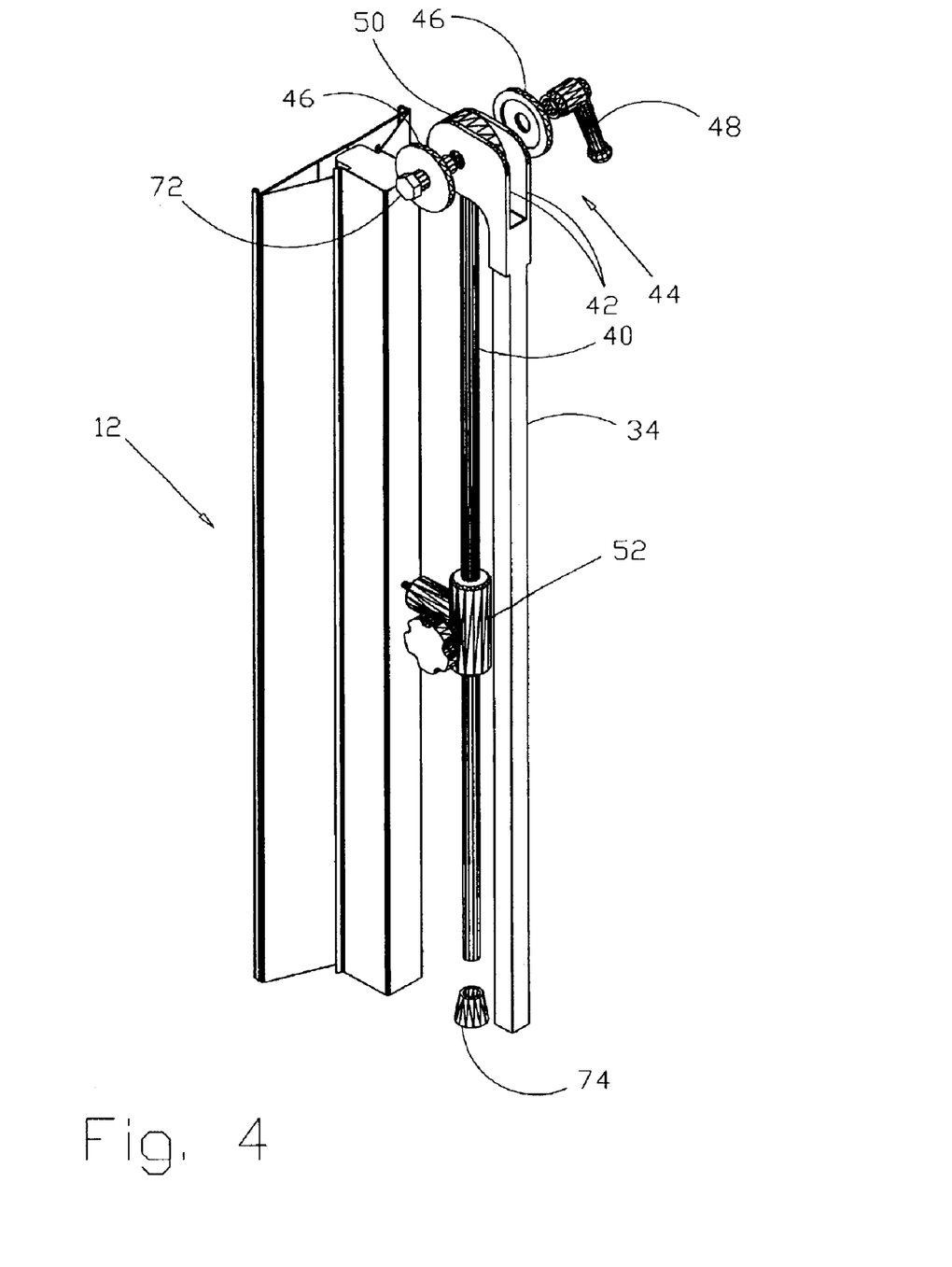
FIG. 4 is an isometric exploded view of light fixture and boom arm and part of the vertical frame and showing the assembly of the boom arm onto the vertical frame stem, the light produced in accordance with the present invention.

The detail of the clamp lock 44 is shown in FIG. 4. The optimal desire of the clamp lock 44 is to provide enough friction between the end disk 50 and the ears 42 to prevent rotation of the boom arm 40. The key elements are the concave pressure plates 46 and the cap handle 48 that work with a threaded fastener 72. The fastener 72 acts as a pivot for the boom arm 40 by the center hole in the end disk 50. The concave aspect of the pressure plates 46 enable the frictional force applied to the ears 42 and the end disk 50 to be concentrated further from the axis, therefore increasing the braking torque at any specific force. This advantage enables the user to easily tighten the cap handle 48 to engage the clamp lock 44 with minimal effort.

At the end of the boom arm 40 is a bumper pad 74 to help prevent damage to a contacted object if the clamp lock 44 was inadvertently disengaged. The bumper pad 74 is preferably a pliable material such as rubber. A "crutch tip" is a common item that can be used in this capacity. The second use of the bumper pad 74 is as a stop to limit the axial displacement of the fixture mount 52 on the boom arm 40.

Figure 5:
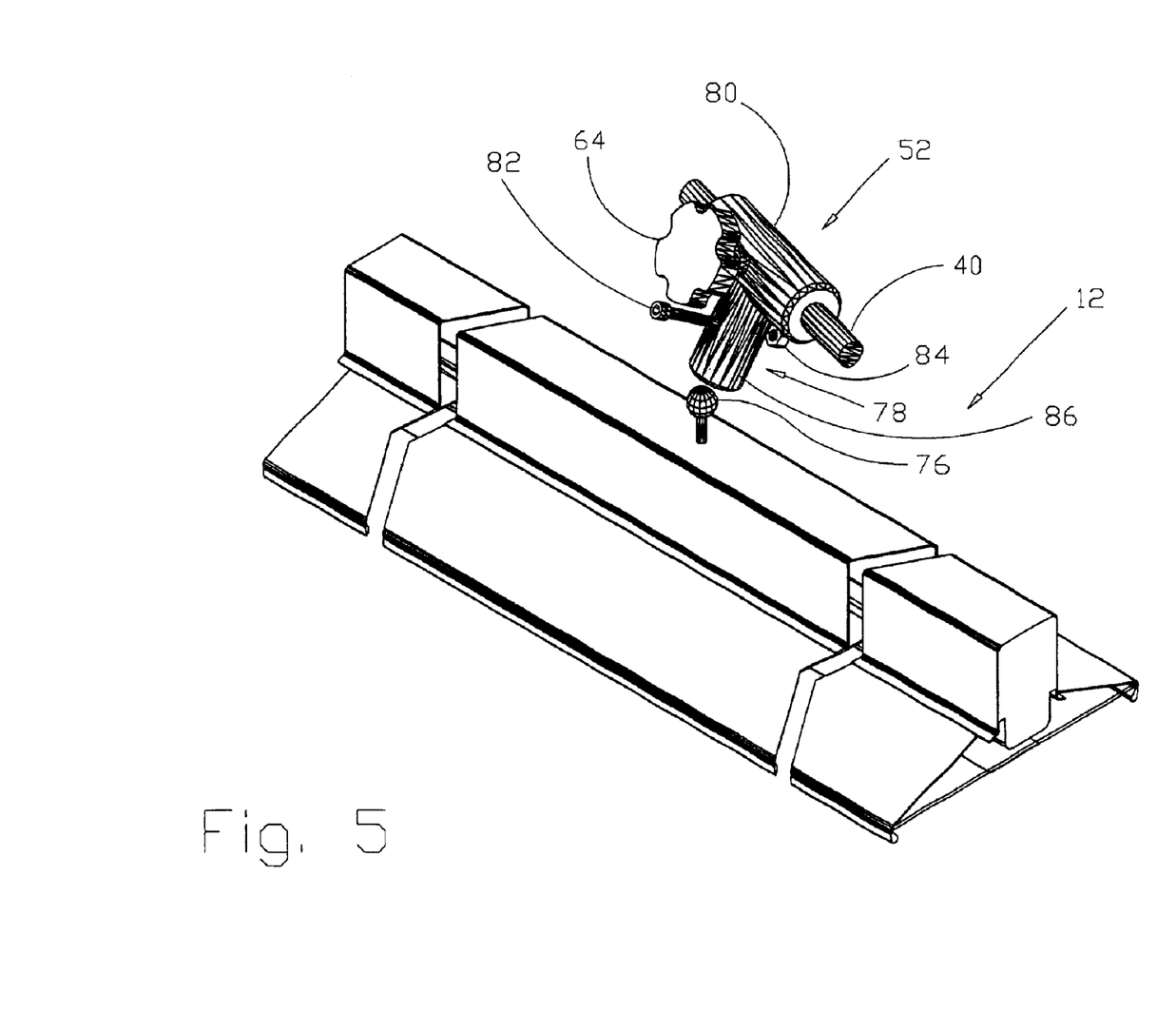
FIG. 5 is an isometric exploded view of truncated light fixture and fixture mount, the light produced in accordance with the present invention.

A detail of the fixture mount 52 is provided in FIG. 5. A ball 76 is mounted to the upper portion of the fixture 12. This remains rigid to the fixture 12 and can be mounted by any means that is known in the art. The mount 52 also includes a hub 78 with a core that is adapted to receive the ball 76. The material of the hub 78 is preferably plastic or some other durable material with good bearing properties. This is advantageous in that the slider 80, which glides on the boom arm 40, can be made of the same material as the hub. This would reduce production costs by eliminating the need for additional bearings. With a low friction material, the normal force of the hub on the ball 76 must be reasonably high to provide enough friction between the hub 78 and the ball 76 to enable movement of the fixture 12 relative to the hub 78 and yet not allow it to move under the weight of the fixture 12. A fastener is used to solve the potential problems of assembly of press fit parts and reduced friction due to wear. A bolt 82 inserts through a hole in the hub 78 and is received by a nut 84. A slit 86 is provided in both sides of the hub 78 to allow for expansion and contraction of the inside dimension of the hub 78, which articulates with the ball 76. This fastener can be tightened or loosened to adjust the friction of the hub 78 against the ball 76 for personal preference and to accommodate wear.

Figure 6:
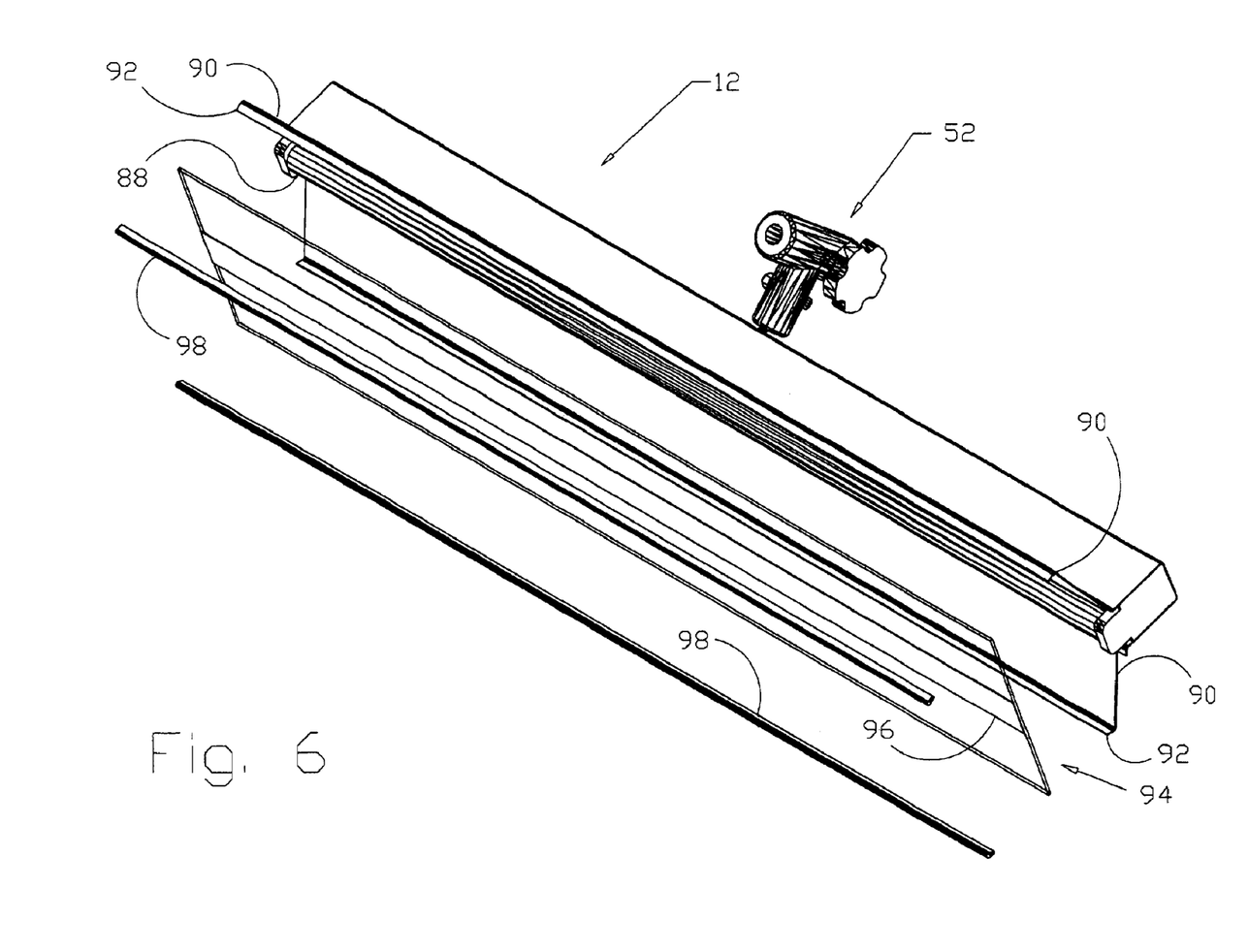
FIG. 6 is an isometric exploded view of a light fixture, the light produced in accordance with the present invention.

A partially exploded view of the fixture 12 is shown in FIG. 6. The fixture 12 includes a bulb 88 such as a florescent or other electric bulb. The shield 90 extends to the side of the bulb 88 and includes a lip 92 on either side to support a lens 94. The lens 94 may be clear or colored. For use in the dent removal process a tinted lens such as yellow or green is many times desirable. An opaque strip 96 is placed in the center of the lens 94. This strip can be a variety of widths but is preferably between 0.75 to 1.25 inches wide and optimally one inch wide. The strip 96 runs the length of the lens 94 and is used to provide additional shadowing to allow better viewing of any dents. Finally a pair of bumper strips 98 is mounted to a peripheral edge of a lamp shield 90. These bumper strips 98 are preferably a soft material similar to the bumper pad 74 earlier noted. The strips 98 can be pressed onto the lips 92 of the shield 90 and held in place by the friction of the materials. The purpose of the strips 98 is to act as a cushion in the event of accidental contact with an object, such as a car body, and to assist in holding the lens 94 in place in the fixture 12.

Figure 7:
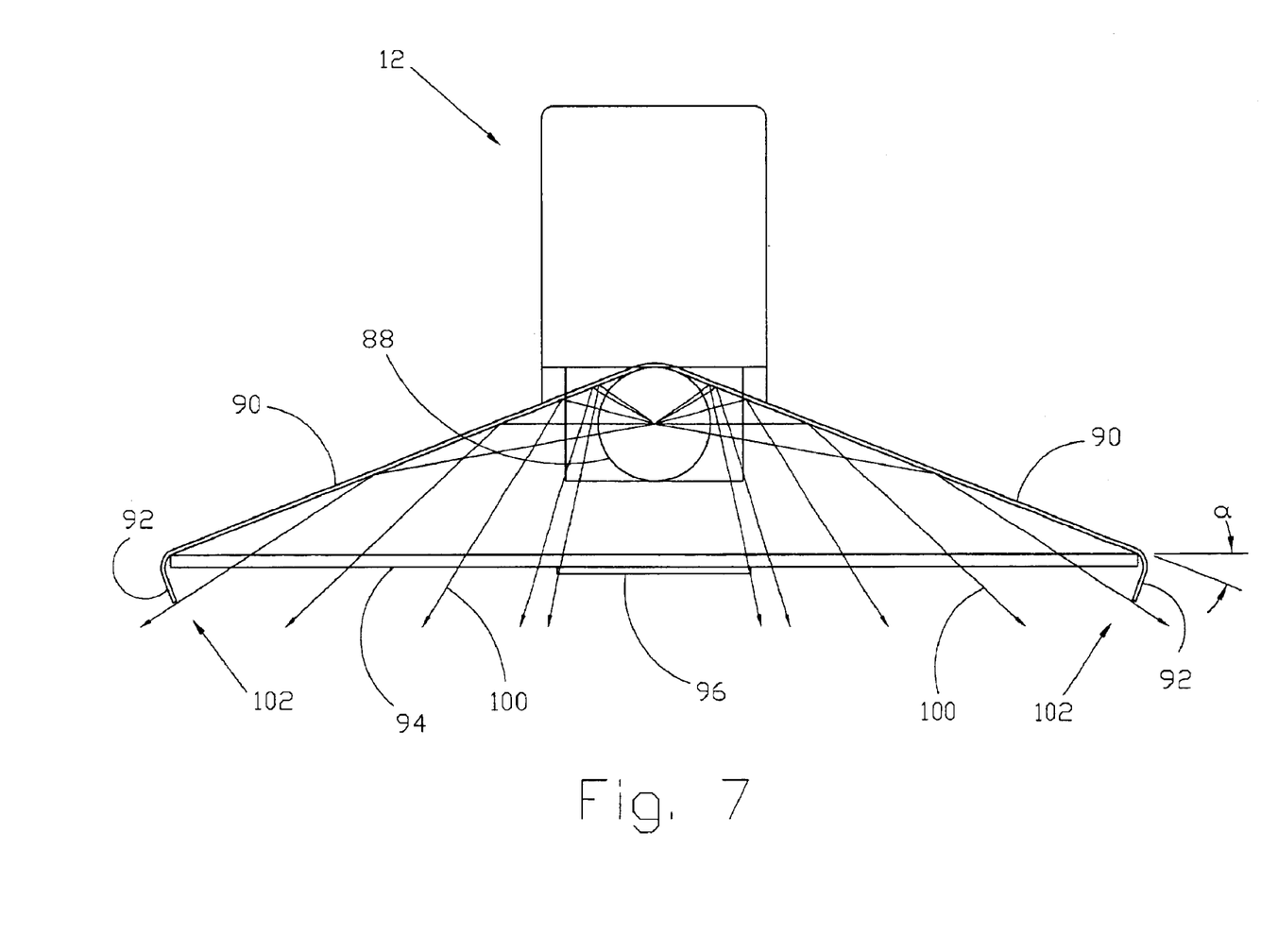
FIG. 7 is a side view of light fixture showing the angles of reflected light rays and opaque area, the light produced in accordance with the present invention.

The fixture 12 is shown in side view in FIG. 7. The lens 94 is positioned within the border of the shield 90 and secured by the lips 92. The strips 98 are not shown in this view, but would be received by the distal end of the lips 92. The opaque strip 96 is exaggerated in its thickness for illustrative purposes. This strip 96 can be a single layer of paint or a layer of material of any thickness. In most cases a coat of paint will be the most cost effective and equally functional.

The reflected light rays 100 being emitted from the bulb 88 are also shown here. These rays 100 are reflected to create a fade effect from the opaque strip 96 located in the center of the lens 94. This is provided by the base angle ($\alpha$) of the shield 90 relative to the lens 94. This angle ($\alpha$) can vary and still provide a desirable effect. The inventor has experimentally determined an optimal range of ($\alpha$) to be between 20° and 30°. Optimally the angle is 25°. This somewhat flattened acute angle provides a diffused effect as the reflected light rays 100 are most intense near the center of the lens, at the edge of the opaque strip 96, and become less intense toward the outside edges 102. This follows as consistent with the direct light from the bulb 88 (not reflected off the shield 90). The closer to the bulb the greater the concentration of the direct rays and therefore the greater the light intensity. Many light shields are commonly made in the form of a parabola with the bulb at the focal point. This creates a directed beam of light, such as in a headlamp. Here the goal is quite different in that the desire is to create a shadowing effect. As such, a diffused light is desirable.

What is claimed is:

1. An adjustable light comprising:
   a base frame;
   an adjustable height vertical frame releasably mounted to said base frame;
   a boom arm pivotally mounted to an upper portion of said vertical frame and including a clamp lock, including a pair of concave pressure plates, a threaded fastener and a cap handle thus providing infinitely adjustable position locking of the boom arm on said vertical frame;
   a light fixture; and
   a fixture mount slideably and rotateably mounted on said boom arm, the fixture mount supporting said tight fixture.

2. A light as in claim 1, wherein said base frame includes at least two legs that are moveably mounted to said base frame.

3. A light as in claim 2, wherein said base frame includes at least two wheels to facilitate transport of said base frame.

4. A light as in claim 2 wherein each of said at least two legs includes a wheel to facilitate transport of said base frame when said legs are mounted thereto.

5. A light as in claim 2, wherein said wheels of said at least two legs can be movably positioned relative to said base frame.

6. A light as in claim 1, wherein said boom arm includes an end disk positioned at one end thereof, the end disk captured between a pair of ears on said vertical frame, said pair of concave pressure plates positioned on the outside of and adjacent to said pair of ears.

7. A light as in claim 1, wherein said light includes a bumper strip mounted to a peripheral edge of a lamp shield.

8. A light as in claim 1, wherein said boom arm includes a bumper pad positioned on a distal end thereof.

9. A light as in claim 1, wherein said fixture mount supports said light fixture by a ball and socket joint.

10. A light as in claim 9, wherein said fixture mount includes a split collar and a tension device enabling adjustable tension on said ball of said ball and socket joint.

11. A light as in claim 10, wherein said tension device is comprised of a threaded fastener.

12. A light as in claim 1, wherein said fixture mount includes a friction lock enabling said fixture mount to be releasably positioned on said boom arm.

13. A light as in claim 1, wherein said light fixture includes a shield with a base angle between 20° and 30° relative to a lens.

14. A light as in claim 13, wherein said base angle is 25°.

15. A light as in claim 1, wherein said light fixture includes a lens with a substantially opaque area in the center thereof and runs the length of said lens.

16. A light as in claim wherein said substantially opaque area is between 0.75 inches and 1.25 inches wide.

17. A light as in claim 16, said substantially opaque are is one inch wide.

18. An adjustable light comprising:
   a base frame;
   an adjustable height vertical frame releaseably mounted to said base frame;
   a boom arm pivotally mounted to an upper portion of said vertical frame and including a clamp lock, including a pair of concave pressure plates, a threaded fastener and a cap handle, thus providing infinitely adjustable position locking of the boom arm on said vertical frame;
   a light fixture; and
   a fixture mount received by said boom arm and supporting said light fixture, the fix mount enabling five degrees of freedom of adjustment of said light fixture relative to said boom arm.

19. A light as claim 18, wherein said base frame includes at least two legs that are movably mounted to said base frame.

20. A light as in claim 19, wherein said base frame includes at least two wheels to facilitate transport of said base frame.

21. A light as in claim 19, wherein each of said at least two legs includes a a wheel to facilitate transport of said base frame when said legs are mounted thereto.

22. A light as in claim 19, wherein said wheels of said at least two legs can be movably positioned relative to said base frame.

23. A light as in claim 18, wherein said boom arm includes an end disk positioned at one end thereof, the end disk captured between a pair of ears on said vertical frame, said pair of concave pressure plates positioned on the outside of and adjacent to said pair of ears.

24. A light as in claim 18, wherein said light includes a bumper strip mounted to a peripheral edge of a lamp shield.

25. A light as in claim 18, wherein said boom arm includes a bumper pad positioned on a distal end thereof.

26. A light as in claim 18, wherein said fixture mount supports said light fixture by a ball and socket joint.

27. A light as in claim 26, wherein said fixture mount includes a split collar and a tension device enabling adjustable tension on said ball of said ball and socket joint.

28. A light as in claim 27, wherein said tension device is comprised of a threaded fastener.

29. A light as in claim 27, wherein said fixture mount includes a friction lock enabling said fixture mount to be releaseably positioned on said boom arm.

30. A light as in claim 18, wherein said light fixture includes a shield with a base angle between 20° and 30° relative to a lens.

31. A light as in claim 18, wherein said base angle is 25°.

32. A light as in claim 18, wherein said light fixture includes a lens with a substantially opaque area in the center thereof and runs the length of said lens.

33. A light as in claim 32, wherein said substantially opaque areas is between 0.75 inches and 1.25 inches wide.

34. A light as in claim 33, wherein said substantially opaque are is one inch wide.

35. A method of using an adjustable light including the steps of:

providing an adjustable light comprising:

a base frame;

an adjustable height vertical frame releaseably mounted to said base frame;

a boom arm pivotally mounted to an upper portion of said vertical frame and including a clamp lock, including a pair of concave plates, a threaded fastener and a cap handle thus providing infinitely adjustable position locking of the boom arm on said vertical frame;

a light fixture; and a fixture mount received by said boom arm and supporting said light fixture, the fixture mount enabling five degrees of from of adjustment of said light fixture relative to said boom arm; adjusting the height of said vertical frame;

arm and said light fixture of said fixture mount.

* * * * *